United States Patent [19]

Wendler et al.

[11] 3,950,359

[45] Apr. 13, 1976

[54] PROSTAGLANDINS AND METHODS OF MAKING SAME

[75] Inventors: Norman L. Wendler, Summit; David Taub, Metuchen, both of N.J.

[73] Assignee: Merck & Co., Inc., Rahway, N.J.

[22] Filed: Dec. 16, 1974

[21] Appl. No.: 533,119

Related U.S. Application Data

[62] Division of Ser. No. 309,389, Nov. 24, 1972, Pat. No. 3,894,052, which is a division of Ser. No. 48,548, June 22, 1970, Pat. No. 3,736,335.

[52] U.S. Cl. .............................................. 260/340.9
[51] Int. Cl.² .......................................... C07D 13/04
[58] Field of Search ................................. 260/340.9

[56] References Cited
UNITED STATES PATENTS 3,833,612   9/1974   Wendler et al. .................. 260/340.9

*Primary Examiner*—Ethel G. Love
*Attorney, Agent, or Firm*—Hesna J. Pfeiffer; Thomas E. Arther; J. Jerome Behan

[57] ABSTRACT

($\pm$)-Prostaglandin $E_1$ is totally synthesized with a high degree of stereoselectivity and in good yield at the various steps from 6-methoxy-3-indanol by a sequence of reactions proceeding through 6-methoxy-3-indeneheptanoic acid ester, 2,6-dioxo-4,5,6,7-tetrahydro-7-methyl-3-indanheptanoic acid ester 2-cyclic ethylene acetal, cis-3,4,5,7a-tetrahydro-7-methyl-2-oxoindanheptanoic acid ester, trans-trans 3-acetyl-2-(2-carboxy-ethyl)-5-oxocyclopentane heptanoic acid ester 5-cyclic-ethylene acetal, 3-acetoxy-2-formyl-5-oxocyclopentaneheptanoic acid ester 5-cyclic ethylene acetal, and 15-dehydro ($\pm$)-prostaglandin $E_1$. The end compound has the biological activity of naturally occurring prostaglandin $E_1$.

4 Claims, No Drawings

PROSTAGLANDINS AND METHODS OF MAKING SAME

CROSS REFERENCES TO RELATED APPLICATIONS

This is a division of application Ser. No. 309,389, filed Nov. 24, 1972, now U.S. Pat. No. 3,894,052, which in turn is a division of U.S. Ser. No. 48,548, filed June 22, 1970, now U.S. Pat. No. 3,736,335, issued May 29, 1973.

BRIEF SUMMARY OF THE INVENTION

This invention relates to a new and novel total synthesis of (±) prostaglandin $E_1$, and more particularly to a total synthesis that has a high degree of stereo-selectivity at the points of generating the asymmetric centers of the molecule. It relates further to a synthesis in which the yields are high in the several reaction steps. The invention relates further to the novel compounds obtained as intermediates in the (±) prostaglandin $E_1$ synthesis, and to the processes for making such intermediates.

DETAILED DESCRIPTION OF THE INVENTION

Prostaglandin $E_1$, which may be depicted structurally as

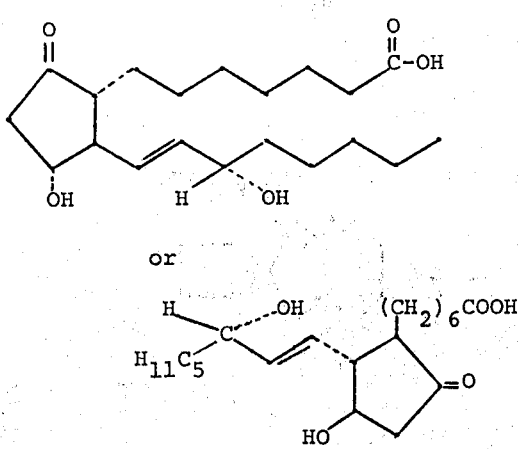

is one of a group of naturally occurring compounds known generally as prostaglandins. These prostaglandins have interesting and important biological activity, the precise biological properties varying with the individual members of the prostaglandin family, as described in the article Prostaglandins, by P. W. Ramwell et al, Progress in the Chemistry of Fats and Other Lipids, Vol. IX, Polyunsaturated Acids, Part 2, pp. 231–273, Pergamon Press (1968).

One of the more important prostaglandins is prostaglandin $E_1$, also known as $PGE_1$. It has an effect on the contractility of smooth muscle and is useful in the induction of labor in pregnant females and for the termination of pregnancy by therapeutic abortion, M. P. Embrey, British Medical Journal, 1970, 2, 256–258; 258–260. Other uses, besides stimulation of smooth muscle, are described in the literature and include lowering of blood pressure, effect on mobilization of free fatty acids from adipose tissue, inhibition of lipolysis, and bronchodilating effect.

Heretofore, the supply of prostaglandin $E_1$, as well as of other prostaglandins, has been severely limited because only minute amounts of naturally occurring material are available, and partial biosynthesis by enzymes present in mammalian seminal vesicles has only afforded limited amounts of the products.

Considerable effort has been directed to chemical synthesis of these materials (Axen, Synthetic Approaches To Prostaglandins, Ann. Reports Med. Chem. 1967, pp. 290–296, Academic Press, 1968), but the syntheses available to date have suffered for the most part from disadvantages of being only partial syntheses, lack of stereospecificity, or of affording analogs instead of the naturally occurring structures.

An object of this invention is to provide a stereoselective total synthesis of (±) prostaglandin $E_1$, which compound has one-half the biological activity of the naturally occurring $PGE_1$, and which may be used for the same biological effects as the natural compounds. This process obviates the disadvantages of the earlier synthetic processes since it is stereoselective, the individual reactions proceed in good yield, and it affords one of the naturally-occurring prostaglandins.

A further object of the invention is to provide novel intermediate compounds some of which, in addition to being useful in the synthesis of (±) $PGE_1$, may themselves exhibit prostaglandin-like activity. An additional object is to provide a stereoselective total synthesis of the other members of the prostaglandin group which may be prepared by known methods from (±) prostaglandin $E_1$. Thus, for instance, (±) prostaglandin $F_{1\alpha}$ may be obtained by reduction of (±) $PGE_1$. Other objects will become evident from the following description of the invention.

The novel process and intermediates of our invention are shown structurally in the following flow diagram, and immediately following this diagram the chemical names of the compounds are set forth.

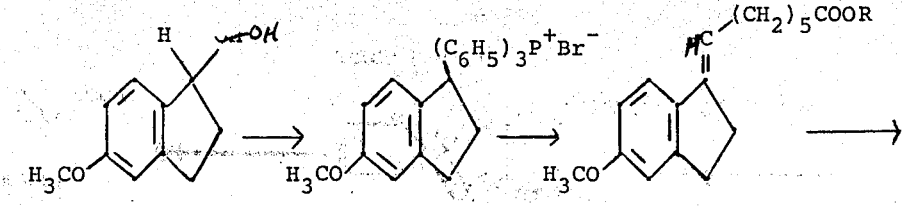

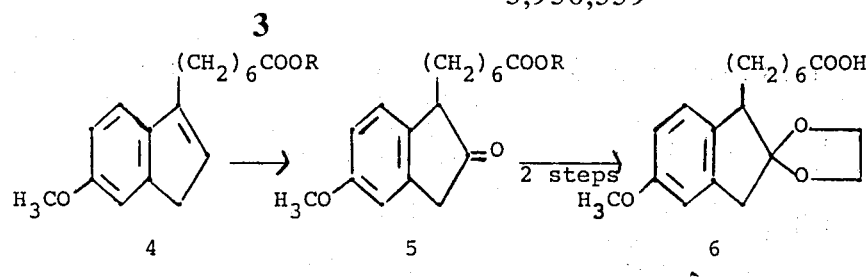
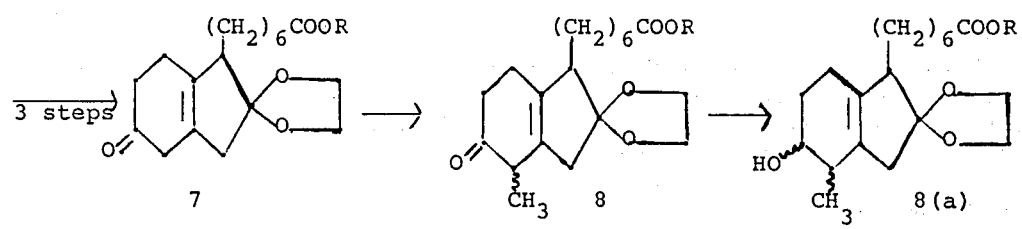
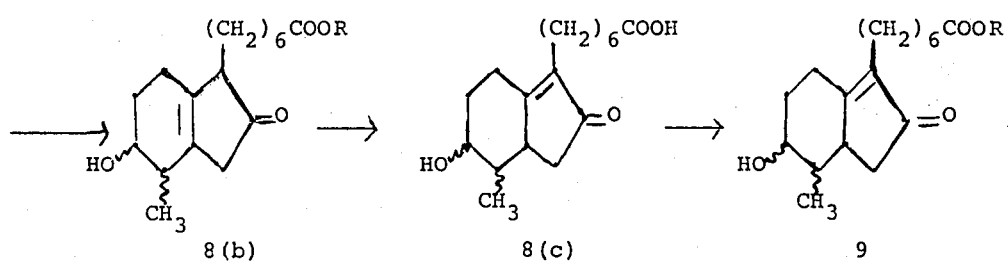
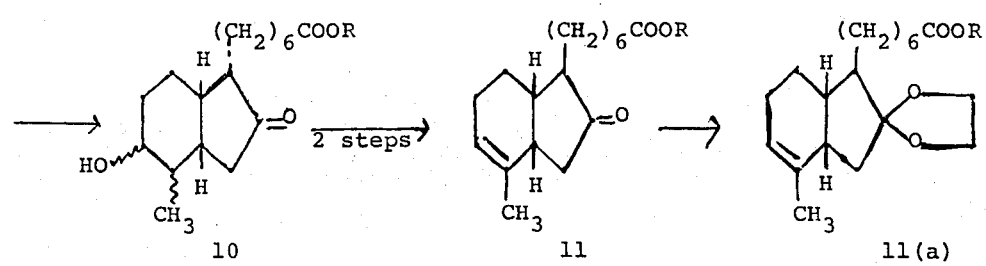
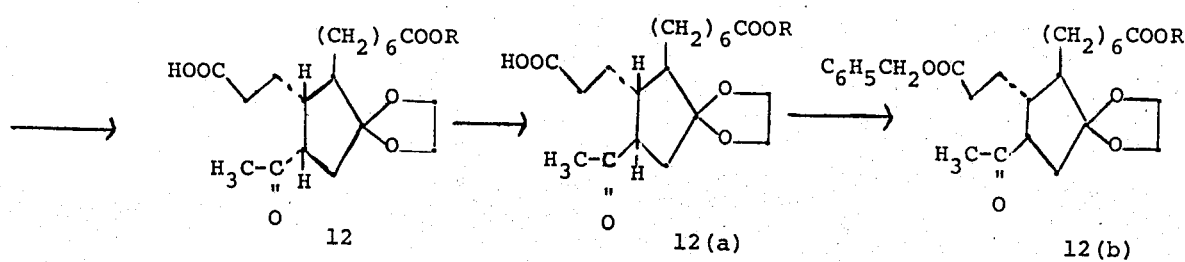
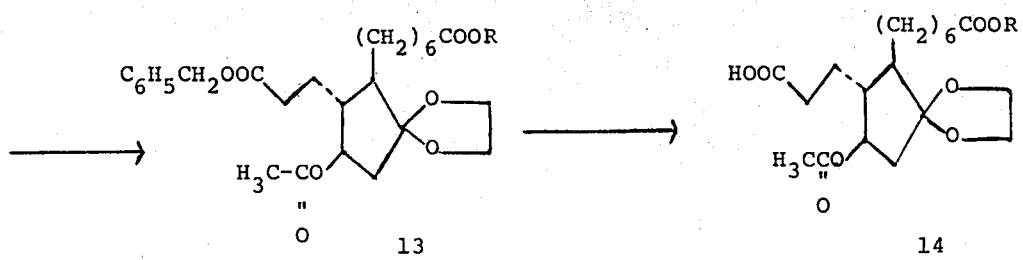

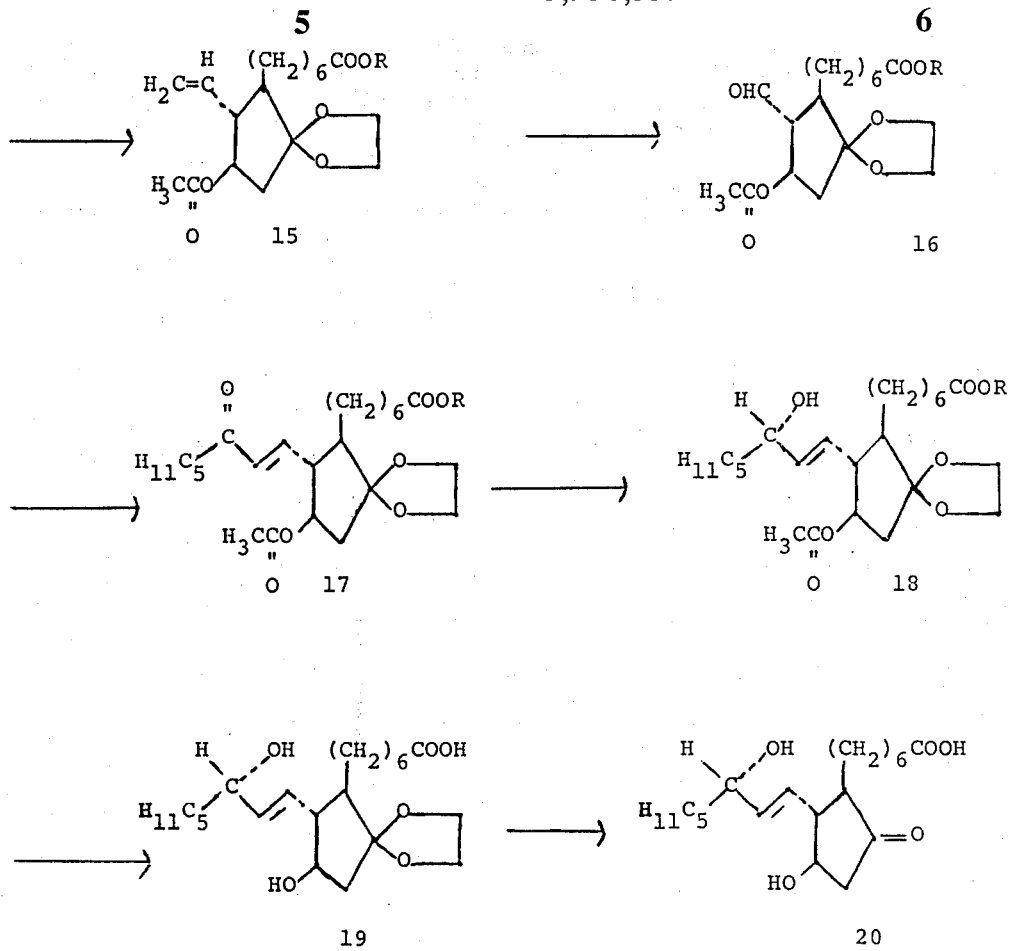

In the foregoing formulas the symbol R represents loweralkyl of about 1-6 carbon atoms such as methyl, ethyl, propyl and hexyl.

As a matter of convenience for understanding the foregoing flowsheet and the following description of the invention there follows a list of the chemical compounds 1-20, inclusive.

1. 6-methoxy-3-indanol
2. (6-methoxy-3-indanyl)triphenylphosphonium bromide
3. 6-methoxy-$\Delta^{3,\omega}$-indanheptanoic acid methyl ester
4. 6-methoxy-3-indeneheptanoic acid methyl ester
5. 6-methoxy-2-oxo-3-indanheptanoic acid methyl ester
6. 6-methoxy-2-oxo-3-indanheptanoic acid, 2-cyclic ethylene acetal
7. 2,6-dioxo-4,5,6,7-tetrahydro-3-indanheptanoic acid methyl ester, 2-cyclic ethylene acetal
8. 2,6-dioxo-4,5,6,7-tetrahydro-7-methyl-3-indeneheptanoic acid methyl ester, 2-cyclic ethylene acetal
8a. 4,5,6,7-tetrahydro-6-hydroxy-7-methyl-2-oxo-3-indeneheptanoic acid methyl ester, 2-cyclic ethylene acetal
8b. 4,5,6,7-tetrahydro-6-hydroxy-7-methyl-2-oxo-3-indeneheptanoic acid methyl ester
8c. 2,4,5,6,7,7a-hexahydro-6-hydroxy-7-methyl-2-oxo-3-indeneheptanoic acid
9. 2,4,5,6,7,7a-hexahydro-6-hydroxy-7-methyl-2-oxo-3-indeneheptanoic acid methyl ester
10. cis-6-hydroxy-7-methyl-2-oxo-3-hydrindanheptanoic acid methyl ester
11. cis-3,4,5,7a-tetrahydro-7-methyl-2-oxoindanheptanoic acid methyl ester
11a. cis-3,4,5,7a-tetrahydro-7-methyl-2-oxoindanheptanoic acid methyl ester, 2-cyclic ethylene acetal
12. 3-acetyl-2-(2-carboxyethyl)-5-oxocyclopentaneheptanoic acid methyl ester, 5-cyclic ethylene acetal (cis-trans)
12a. 3-acetyl-2-(2-carboxyethyl)-5-oxocyclopentaneheptanoic acid methyl ester, 5-cyclic ethylene acetal (trans-trans)
12b. 3-acetyl-2-[2-(benzyloxycarbonyl)ethyl]-5-oxocyclopentaneheptanoic acid methyl ester, 5-cyclic ethylene acetal
13. 3-acetoxy-2-[2-(benzyloxycarbonyl)ethyl]-5-oxocyclopentanehaptanoic acid methyl ester, 5-cyclic ethylene acetal
14. 3-acetoxy-2-(2-carboxyethyl)-5-oxocyclopentaneheptanoic acid methyl ester, 5-cyclic ethylene acetal
15. 3-acetoxy-2-vinyl-5-oxocyclopentanehaptanoic acid methyl ester, 5-cyclic ethylene acetal 16. 3-acetoxy-2-formyl-5-oxocyclopentaneheptanoic acid methyl ester, 5-cyclic ethylene acetal
17. 3-acetoxy-2-(3-oxo-1-octenyl)-5-oxocyclopentaneheptanoic acid methyl ester, 5-cyclic ethylene acetal
18. 3-acetoxy-2-(3-hydroxy-1-octenyl)-5-oxocyclopentaneheptanoic acid methyl ester, 5-cyclic ethylene acetal
19. 3-hydroxy-2-(3-hydroxy-1-octenyl)-5-oxocyclopentaneheptanoic acid, 5-cyclic ethylene acetal
20. 3-hydroxy-2-(3-hydroxy-1-octenyl)-5-oxocyclopentane heptanoic acid In the foregoing list of names the esters have been referred to as methyl esters because the detailed examples refer to such esters, but it is to be understood that other esters, and preferably loweralkyl esters, are within the scope of the invention as shown by the symbol R in the flow diagram.

In the first step of our invention 6-methoxy-3-indanol is reacted with a trialkylphosphonium hydrobromide, or, preferably, triphenylphosphine hydrobromide in order to produce (6-methoxy-3-indanyl)triphenylphosphonium bromide (Compound 2). The reaction is conveniently carried out at about room temperature for from 1½ to 3 hours in the presence of an organic solvent such as methylene chloride, chloroform, or tetrahydrofuran. The resulting product is next reacted with a loweralkyl-6-formylhexanoate, such as methyl, ethyl or propyl 6-formylhexanoate, in the presence of reagents suitable for use in a Wittig coupling reaction such as in a system comprising potassium t-butoxide-dimethylsulfoxide, sodium hydride-dimethylsulfoxide or alkali metal alkoxide-t-butanol or tetrahydrofuran. This reaction is also conducted at about room temperature and is generally substantially complete in from 30–90 minutes. There is obtained a loweralkyl ester of 6-methoxy-$\Delta^{3,\omega}$-indanheptanoic acid such as 6-methoxy-$\Delta^{3,\omega}$-indanheptanoic acid methyl ester (Compound 3). This material is then isomerized directly to 6-methoxy-3-indeneheptanoic acid methyl ester, or other loweralkyl ester (Compound 4), by contacting it with a strong acid in suitable solvent. Trifluoroacetic acid is the preferred isomerization acid but others such as dilute aqueous hydrochloric acid or p-toluenesulfonic acid may be used if desired. Examples of solvents which are suitable are chloroform, acetone, methanol, and benzene, acetone and methanol being used when hydrochloric acid is the catalyst. The time and temperature for the isomerization are not unduly critical, satisfactory results being obtained at room temperature in from about 2–6 hours.

The 6-methoxy-3-indeneheptanoic acid methyl ester, or other loweralkyl ester, thus obtained is next converted to 6-methoxy-2-oxo-3-indanheptanoic acid methyl ester, or other esters (Compound 5), by reacting it with osmium tetroxide in the presence of a solvent such as pyridine. The reaction is conveniently conducted at about room temperature for from 12–24 hours and the resulting osmate ester decomposed for from 12–24 hours and the resulting osmate ester decomposed with reagents known for this purpose such as sodium bisulfite. The resulting glycol is dehydrated to the ketone (Compound 5) by treatment with an acid such as p-toluenesulfonic acid, trifluoroacetic acid, or hydrogen chloride in a suitable solvent such as benzene, methanol, dioxane, or chloroform.

Compound 5 is, in the next reaction sequence of the process of our invention, converted in two steps to 6-methoxy-2-oxo-3-indanheptanoic acid, 2-cyclic ethylene acetal (Compound 6). In the first of these two steps the keto-ester Compound 5 is treated with ethylene glycol in the presence of an acid catalyst such as p-toluenesulfonic acid in a suitable water-immiscible solvent such as benzene and the mixture heated for from 12–24 hours to afford the cyclic ethylene acetal. Water is continuously removed during the reaction. This latter product is then treated with a strong base in an aqueous lower alkanol in order to saponify the ester group and afford 6-methoxy-2-oxo-3-indanheptanoic acid, 2-cyclic ethylene acetal. As the base, there may be employed potassium hydroxide or sodium hydroxide in a solvent such as methanol, ethanol or isopropanol.

In the next stage of the process of this invention 6-methoxy-2-oxo-3-indanheptanoic acid, 2-cyclic ethylene acetal is converted in three steps to 2,6-dioxo-4,5,6,7-tetrahydro-3-indanheptanoic acid loweralkyl ester, 2-cyclic ethylene acetal (Compound 7). The first of these steps comprises the Birch reduction of Compound 6 preferably using lithium-liquid ammonia, although reagents such as sodium-liquid ammonia or lithium-methylamine could be employed if desired. The reduction is substantially complete in about 3–5 hours at the reflux temperature of the preferred ammonia tetrahydrofuran-t-butanol solvent system. The resulting free acid is then esterified with a diazoloweralkane to form a loweralkyl ester, suitable esters being methyl, ethyl and propyl. The methyl ester is preferred and is frequently referred to hereinbelow, but it is to be understood that other loweralkyl esters may also be utilized equally well throughout the synthesis. The diazoalkane esterification is conveniently brought about in ether at about room temperature for from 5 to 20 minutes, utilizing a molar excess of the esterifying agent. The resulting ester is then treated with aqueous acetic acid in the cold (5°–15°C.) and the reaction allowed to proceed at this temperature for from 4–7 hours. Although other weak acids such as propionic acid or aqueous oxalic acid may be used, the aqueous acetic acid system is preferred. The resulting 2,6-dioxo-4,5,6,7-tetrahydro-3-indanheptanoic acid methyl ester, 2-cyclic ethylene acetal (Compound 7) is recovered by known techniques such as extraction into a water-immiscible organic solvent followed by removal of such solvent.

Compound 7 is next selectively methylated at the 7-position by forming an alkali metal enolate under aprotic conditions and then treating the enolate with methyl iodide. It is preferred to use lithium triphenylmethyl in a solvent system consisting of hexamethylphosphortriamide and tetrahydrofuran as the enolating agent although the bromo magnesium enolate of acetomesitylene or any alkali metal alkane that connot add to a carbonyl group such as sodium triphenylmethyl in ether, could be used, in each case methyl iodide being used to effect the desired methylation. The reaction proceeds rapidly and satisfactory results have been obtained is from 3-10 minutes at room temperature. At the end of the reaction period 2,6-dioxo-4,5,6,7-tetrahydro-7-methyl-3-indeneheptanoic acid methyl ester, 2-cyclic ethylene acetal or other loweralkyl ester (Compound 8) is recovered by extraction into a water-imiscible organic solvent and, if necessary, chromatographed over an adsorbent such as silica gel.

In the next reaction step of our invention, the 3-indeneheptanoic acid loweralkyl ester obtained as described immediately above is reduced with lithium tri-t-butoxy aluminum hydride, preferably in the cold, over a period of from 2–6 hours in order to convert the ketone at the 6 position to a hydroxy group and produce 2-oxo-4,5,6,7-tetrahydro-6-hydroxy-7-methyl-3-indeneheptanoic acid loweralkyl ester, 2-cyclic ethylene acetal (Compound 8a). Other lithium trialkoxy aluminum hydrides, such as the trimethoxy, could also be used to reduce the ketone, as could sodium borohydride. A mixture of epimeric 6-hydroxy compound is produced, and this mixture is carried through the reaction sequence until the 6-hydroxy group is removed in a later stage of our novel process.

Upon completion of the foregoing reduction, the cyclic ethylene acetal blocking group at the 2-position is removed by reaction with an acid such as aqueous perchloric acid at temperatures from about 5°–20°C. for 1–3 hours to provide the free ketone (Compound 8b). Alternatively, aqueous acetic acid at elevated temperatures or aqueous hydrochloric acid in a solvent such as methanol at oven temperature could be employed to regenerate the ketone.

The ensuing reaction of our process comprises the isomerization of the double bond in Compound 8b to Compound 8c. This isomerization is brought about with a base such as sodium or potassium hydroxide in a lower-alkanol, the reaction conveniently being carried out at about room temperature for from about 10–30 hours. During this step the loweralkyl ester is also saponified to the corresponding free acid, and it is necessary to reform the ester for the ensuing transformations. The next step of the process, therefore, comprises re-esterification to afford 2,4,5,6,7,7a-hexahydro-6-hydroxy-7-methyl-2-oxo-3-indeneheptanoic acid loweralkyl ester (Compound 9). The esterification is brought about by treating the free acid with a diazoalkane such as diazomethane or diazoethane. It is preferred to produce the methyl ester using diazomethane in ether. Alternatively, the isomerization of Compound 8b to 8c can be brought about by using an alkali metal alkoxide, preferably sodium methoxide, as the base in which case the ester group is not removed and the esterification step described immediately above becomes unnecessary.

The next reaction in our total synthesis of (±) prostaglandin $E_1$ comprises the reduction of Compound 9 to cis-6-hydroxy-7-methyl-2-oxo-3-hydrindanheptanoic acid loweralkyl ester (Compound 10). This conversion is brought about by catalytic hydrogenation using a palladium catalyst and employing as solvent a loweralkanol such as methanol or ethanol. The reaction proceeds smoothly at about atmospheric pressure and room temperature, although higher temperatures and pressures could be used, if desired. This reduction may also be carried out on the free acid (instead of the ester) and in this event the reduced product is esterified with a diazoalkane before proceeding with the next step of our process. An important and critical feature of this catalytic hydrogenation reaction is its stereospecificty since the product obtained (Compound 10) is in the necessary cis configuration. It will be appreciated by those skilled in this art that this stereospecificity is essential at this stage of our process in order to assure the proper orientation of the C-3 side chain and the correct stereochemical course of subsequent reactions.

The next stage of our process involves introduction of a double bond between the 6 and 7 carbon atoms of the molecule. This is accomplished by first reacting cis-6-hydroxy-7-methyl-2-oxo-3-hydrindanheptanoic acid loweralkyl ester (Compound 10) with a loweralkanesulfonyl halide or a substituted phenylsulfonyl halide in the presence of an appropriate organic base, and treating the resulting ester with dimethyl sulfoxide or sulfolane. It is preferred to use a methanesulfonyl chloride pyridine system at 0°–10°C. to obtain the 6-mesylate derivative of Compound 10, although satisfactory results can be obtained using p-nitrophenylsulfonyl chloride or p-toluenesulfonyl chloride at room temperature in the presence of a base such as pyridine, a picoline, or trimethylamine. The second reaction, i.e. of the 6-sulfonate with dimethyl sulfoxide or sulfolane is brought about at elevated temperatures of about 80°–100°C. for from 2–10 hours, at the end of which time the desired product cis-3,4,5,7a-tetrahydro-7-methyl-2-oxoindaneheptanoic acid methyl ester, or other loweralkyl ester, (Compound 11) is recovered and purified by techniques known to those skilled in this art such as extraction into and recovery from a water immiscible organic solvent and chromatography on a suitable adsorbent such as silica gel. In this reaction the heptanoic acid side chain is isomerized to give predominantly the 3-exo isomer, which is important to the stereoselective nature of our total synthesis.

Prior to the next substantive step of our process the keto-ester (Compound 11) is converted to the corresponding cyclic ethylene acetal (Compound 11a) by reaction with ethylene glycol in the presence of an acid such as p-toluene sulfonic acid. The resulting acetal is then oxidized with potassium permanganate preferably in the presence of sodium periodate to produce the seco acid cis-trans 3-acetyl-2-(2-carboxyethyl)-5-oxocyclopentaneheptanoic acid loweralkyl ester, 5-cyclic ethylene acetal (Compound 12). If desired the sodium periodate can be omitted from this reaction system but such omission requires the use of larger quantities of potassium permanganate and therefore is not a preferred aspect of the invention. The reaction proper affords predominantly the cis-trans isomer as depicted in the foregoing flow sheet as Compound 12. It is preferred, however, to conduct the oxidation in the presence of potassiuum carbonate. The potassium carbonate facilitates the reaction and incidentally partially epimerizes the cis-trans epimer to the more stable trans-trans epimer so that the immediate reaction product is a mixture of the two epimers.

In the next stage of this invention, the foregoing mixture of epimers is reacted with an alkali metal alkoxide such as sodium methoxide or ethoxide in a loweralkanol in order to complete the isomerization to the desired trans-trans material (Compound 12a). The choice of alkoxide is not critical, although it should correspond to the ester present in Compound 12 in order to avoid ester interchange. The reaction is conveniently carried out at about room temperature for from 10–20 hours and the resulting trans-trans keto acid (Compound 12a) then esterified with phenyldiazomethane or a substituted phenyl diazomethane or a substituted phenyl diazomethane to produce the corresponding benzyl ester 3-acetyl-2-[2-(benzyloxycarbonyl)ethyl]-5-oxocyclopentaneheptanoic acid loweralkyl ester, 5-cyclic ethylene acetal (Compound 12b) which is required for the next substantive reaction.

The benzyl or substituted benzyl ester obtained as described above (Compound 12b) is treated with an organic peracid under Bayer-Villiger oxidation conditions to afford 3-acetoxy-2-[2-(benzyloxycarbonyl)ethyl]-5-oxocyclopentaneheptanoic acid loweralkyl ester, 5-cyclic ethylene acetal (Compound 13). It is preferred to use trifluoroperacetic acid as the oxidant although other peracids such as peracetic acid and m-chloroperbenzoic acid may be employed. The reaction mixture is buffered with a weakly basic inorganic salt such as sodium bicarbonate or disodium hydrogen phosphate in order to preclude loss of the cyclic acetal radical. The reaction is preferably carried out at about room temperature for from 5-30 hours at the end of which time the desired product is recovered by techniques known to those skilled in the art. It should be noted that in this reaction the stereochemical configuration at the center of oxygen insertion is retained, and correspondingly that of the molecule as a whole.

The benzyl ester (Compound 13) is next subjected to hydrogenolysis to produce 3-acetoxy-2-(2-carboxyethyl)-5-oxo-cyclopentaneheptanoic acid loweralkyl ester, 5-cyclic ethylene acetal (Compound 14). This hydrogenolysis is conveniently carried out at atmospheric pressure and at about room temperature in the presence of palladium catalyst and in a suitably inert organic solvent such as ethyl acetate, ethanol, benzene or dioxane.

Compound 14 is, in the next aspect of our process, oxidatively decarboxylated to afford 3-acetoxy-2-vinyl-5-oxo-cyclopentaneheptanoic acid loweralkyl ester, 5-cyclic acetal (Compound 15) examples of suitable esters being the methyl, ethyl or propyl esters. This reaction is brought about by treating the starting material with lead tetraacetate in pyridine to induce formation of the lead salt of the carboxylic acid, followed by copper acetate, and exposing this material to irradiation with ultraviolet light in the range of 3,000–3,500 Angstrom units. The light reaction is essentially complete in about 1½ – 4 hours at 25°–35°C. Alternatively, instead of ultraviolet light, the second phase of this reaction may be effected by heating the mixture in benzene at about 75°–80°C.

The 2-vinyl compound (Compound 15) is then converted to the corresponding 3-acetoxy-2-formyl-5-oxocyclopentanehpetanoic acid loweralkyl ester, 5-cyclic ethylene acetal (Compound 16) by reaction with osmium tetroxide and sodium periodate in a solvent system such as aqueous tetrahydrofuran, aqueous ether or aqueous dioxane. It is necessary to use only a catalytic amount of osmium tetroxide since that reagent is continuously regenerated by the periodate which also cleaves the glycol formed by osmium tetroxide. Satisfactory results are obtained by carrying out the reaction at about room temperature for 1 to 3 hours.

In the next step of this process 3-acetoxy-2-(3-oxo-1-octenyl)-5-oxocyclopentane heptanoic acid loweralkyl ester, 5-cyclic ethylene acetal (Compound 17) is obtained by reacting together 3-acetoxy-2-formyl-5-oxocyclopentane heptanoic acid loweralkyl ester, 5-cyclic ethylene acetal (Compound 16) with a diloweralkyl-2-oxo-heptylphosphonate under Wittig conditions. It is preferred to use a dimethyl or diethyl phosphonate but other dialkyl phosphonates such as the di-m-propyl or dibutyl would be satisfactory. The reaction is carried out in the presence of sodium hydride at about room temperature for 2-4 hours. Triphenyl or trialkylphosphonium yields may be used in place of the dialkyl phosphonate but the latter is preferred. The reaction is normally conducted in tetrahydrofuran, although other solvents such as dioxane or dimethoxyethane could be used if desired.

In the next reaction of our invention, Compound 17 obtained as described above is reduced with sodium borohydride to afford 3-acetoxy-2-(3-hydroxy-1-octenyl)-5-oxocyclopentaneheptanoic acid methyl ester, 5-cyclic ethylene acetal (or other lower alkyl ester) (Compound 18) as a mixture of 2 epimers at the point of reduction. The reaction is carried out in an inert solvent medium such as a loweralkanol or tetrahydrofuran, and potassium or calcium borohydride. The mixture of epimers may be resolved at this stage of the process by chromatography on silica gel, or the separation may be deferred until a subsequent point in the synthesis.

In the preferred aspect of the invention, the mixture of epimers obtained immediately above (Compound 18) is treated with an alkali metal hydroxide such as sodium or potassium hydroxide in an aqueous loweralkanol to convert the loweralkyl ester (Compound 18) to the corresponding free acid Compound 19. The saponification is conveniently brought about at temperatures of from about 20°–35°C. in about 2–4 hours. If desired, the epimeric mixture may be separated at this stage but it has been found most convenient to defer the separation until after the next reaction.

The final step of our stereospecific synthesis of (±) prostaglandin $E_1$ comprises removal of the cyclic ethylene acetal blocking group by treating Compound 19 with aqueous acetic acid at a pH of from 4.5–5.5 at a temperature of from about 10°–40°C. Other acidic systems could be used instead of the aqueous acetic acid but they should be in the pH 4.5–5.5 range since this pH control is important in order to retain the rest of the molecule intact on completion of the ketone regeneration. The material thus obtained is chromatographed on silica gel and the more polar material separated to afford (±) 3-hydroxy-2-(3-hydroxy-1-octenyl)-5-oxocyclopentaneheptanoic acid, i.e. (±) prostaglandin $E_1$. This material possesses one-half of the biological activity of the naturally occurring (−) prostaglandin $E_1$.

The following examples illustrate methods of carrying out the present invention but it is to be understood that these examples are given for purposes of illustration and not of limitation.

EXAMPLE 1

(6-Methoxy-3-indanyl)-triphenylphosphonium bromide

To a clear, stirred solution of 50 g. (0.3049 moles) of 6-methoxy-3-indanol in 750 mls. of methylene chloride, contained in a 2-liter, single neck, round bottom flask 102.3 g. (0.3049 moles) of triphenylphosphine hydrobromide are added in portions over 5 minutes. Stirring, at room temperature, of the clear yellow solution is continued for one hour. The reaction mixture is then concentrated to dryness on the water pump yielding a rigid foam.

250 Mls. of acetone are added to the foam. The foam dissolves completely, and almost immediately a white powdery solid starts to precipitate. After the mixture is stirred for 30 minutes in an ice-bath, the solid is filtered, washed twice with cold acetone and partially dried in air. The product is dried in a vacuum oven at 40°C. to constant weight to afford 6-methoxy-3-indanyl-triphenylphosphonium bromide (Compound 2) as a white solid, m.p. 210°–212°C.

EXAMPLE 2

6-Methoxy-3-indeneheptanoic acid methyl ester

To a stirred solution of 9.625 g. of potassium t-butoxide in 60 ml. of dimethylsulfoxide is added dropwise a solution of 40 g. of the phosphonium salt of Example 1 in 300 ml. of dimethylsulfoxide. After six minutes an equimolar amount (12.93 g.) of methyl-6-formylhexanoate is added dropwise just discharging the red color of the reaction mixture. The mixture is stirred for 1 hour at room temperature, and then poured into 1 liter of ice-water and 350 ml. of hexane. It is shaken, the white triphenylphosphine oxide is filtered off and the aqueous layer is extracted with ten 75 ml. portions of hexane. The combined hexane extracts are succcessively washed with four 250 ml. portions of (1:1) dimethylsulfoxide-water, four portions of water and one 300 ml. portion of saturated salt solution. After drying over magnesium sulfate the hexane mixture is concentrated to a yellow oil containing 6-methoxy-$\Delta^{3,\omega}$-indanheptanoic acid methyl ester (Compound 3). The yellow oil is dissolved in chloroform (200 ml.) and to this is added 5 drops of trifluoroacetic acid. The mixture is allowed to stand at room temperature for 4.5 hours and then concentrated to dryness in vacuo. Upon trituration with hexane (15 ml.) 6-methoxy-3-indeneheptanoic acid methyl ester (Compound 4) separates in cystalline form, m.p. 30°–31.5°C.

EXAMPLE 3

6-Methoxy-2-oxo-3-indanheptanoic acid methyl ester

To 10.25 g. of 6-methoxy-3-indeneheptanoic acid methyl ester (Compound 4) in 40 ml. of dry pyridine is added at 15°–18°C. with stirring and cooling a solution of 9.0 g. of osmium tetroxide in 60 ml. of pyridine. The mixture is stirred at room temperature for 18 hours and added with stirring to a solution of 16.2 g. of sodium bisulfite in 270 ml. of water and 180 ml. of pyridine at about 18°C. The mixture is allowed to warm to room temperature (25°C.) and stirred for 1 hour. To this mixture is added 500 ml. of chloroform and 500 ml. of water and the layers are shaken and separated. The water layer is extracted with four 250 ml. portions of chloroform and the combined chloroform extracts extracted with ice cold 2.5 N hydrochloric acid until the aqueous phase is pH 2. The chloroform layer is washed successively with 5% sodium bicarbonate, water and saturated salt solution, dried over MgSO$_4$ and concentrated to an oil in vacuo. The glycol ester is used directly in the next step.

A solution of glycol ester from the previous step in 50 ml. of benzene is added dropwise with stirring to a solution of 6.5 g. of anhydrous p-toluenesulfonic acid in 10 ml. of benzene. The mixture is stirred at room temperature for 4 hours, decanted and the solid washed with benzene. The combined benzene extracts are washed successively with 5% potassium bicarbonate, water and saturated salt solution, dried over MgSO$_4$ and charcoal and concentrated in vacuo to an oil which crystallizes. The product is triturated with etherhexane (1:1) and dried to afford 6-methoxy-2-oxo-3-indanheptanoic acid methyl ester, m.p. 33.5–35°C.

EXAMPLE 4

6-Methoxy-2-oxo-3-indanheptanoic acid, 2-cyclic ethylene acetal

A mixture of 16.5 g. of 6-methoxy-2-oxo-3-indanheptanoic acid methyl ester, 650 ml. of benzene, 24 ml. of ethylene glycol (24.0 ml.) and 0.36 g. of p-toluenesulfonic acid in a flask equipped with a condenser and water separator is heated with stirring to reflux under a nitrogen atmosphere. Reflux with stirring is continued for 22 hours at the end of which the mixture is allowed to cool under nitrogen. The mixture is chilled to 6°C., an excess of 5% aqueous potassium carbonate is added. The benzene layer is extracted successively with three 250 ml. portions of water and one of saturated salt solution, dried over Na$_2$SO$_4$ and concentrated to an oil in vacuo. The total concentrate of 6-methoxy-2-oxo-3-indanheptanoic acid methyl ester, 2-cyclic ethylene acetal is used directly in the next step.

B. The ester of the previous step is dissolved in 175 ml. of methanol under nitrogen and a chilled solution of 5.3 g. of potassium hydroxide in 88 ml. of methanol-water (3:1) is added dropwise with stirring. The mixture is stirred for 2.5 hours and allowed to stand overnight at room temperature (25°C.). The mixture is then concentrated to small volume in vacuo, diluted with ice-water and extracted with two 60 ml. portions of benzene-hexane (1:1).

To the aqueous phase is added 200 ml. of chloroform and then 10% aqueous monosodium phosphate with stirring to pH 6. The water layer is extracted with four 100 ml. portions of chloroform and the combined chloroform extracts extracted with one 200 ml. portion of water and one of saturated salt solution. The chloroform extract is dried over Na$_2$SO$_4$, filtered through 12 g. of silica gel and concentrated to an oil in vacuo which is substantially pure 6-methoxy-2-oxo-3-indanheptanoic acid, 2-cyclic ethylene acetal by thin layer chromatography. This material is used directly in the following step.

EXAMPLE 5

2,6-Dioxo-4,5,6,7-tetrahydro-3-indanheptanoic acid methyl ester, 2-cyclic ethylene acetal 11.32 g. of the ketal acid of Example 4 is dissolved in 290 ml. of tetrahydrofuran and dry t-butanol (1:1) and the solution is added dropwise with stirring and cooling to 290 ml. of liquid ammonia. 4.045 g. of lithium wire is immersed in hexane to free it from grease, then added in strips about 1.5 inches long to the reaction mixture with stirring. The addition takes place over 4 hours during which the mixture gently refluxes. After 15 minutes of additional stirring 25 ml. of methanol is added to discharge the blue color, followed by 80 ml. more of methanol. Nitrogen is slowly passed over the mixture to sweep out most of the ammonia over a period of 18 hours.

The mixture is diluted with 250 ml. of water and concentrated using an aspirator to remove ammonia, concentrated in vacuo to remove tetrahydrofuran and t-butanol. 100 Ml. of water is added to the concentrate and the mixture is extracted with two 100 ml. portions of ether. To the alkaline aqueous layer is added with stirring 150 ml. of cold chloroform and ice-cold 10% aqueous monosodium phosphate to pH 5.5. The layers are separated and the water phase is extracted with four 100 ml. portions of chloroform. The combined chloroform extracts are washed in turn with two 150 ml. portions of water and one 200 ml. portion of saturated salt solution, dried over Na$_2$SO$_4$ and concentrated to an oil in vacuo. The product weighs 11.15 g. and is used directly in the next step.

To the oil from the previous step in 25 ml. of ether there is added dry ethereal diazomethane until no bubbling is seen. After 15 minutes, with an excess of diazomethane present, the mixture is swept with nitrogen and then concentrated to an oil in vacuo. The product weighs 11.3. g. and is used directly in the next step.

To 9.4 g. of the ketal ester obtained immediately above in 18 ml. of tetrahydrofuran is added dropwise at 10°C. 108 ml. of acetic acid-water (1:1). The stirring at 10°C. is continued under nitrogen for 5.25 hours. The reaction mixture is poured into an excess of ice-cold potassium bicarbonate solution and the mixture extracted with three 300 ml. portions of benzene-hexane (9:1). The benzene extracts are washed successively once each with water and saturated salt solution, dried over Na$_2$SO$_4$ and concentrated to dryness in vacuo to afford 2,6-dioxo-4,5,6,7-tetrahydro-3-indanheptanoic acid methyl ester, 2-cyclic ethylene acetal, ir(neat) 5.75, 5.82, 10.50$\mu$.

EXAMPLE 6

2,6-Dioxo-4,5,6,7-tetrahydro-7-methyl-3-indanheptanoic acid methyl ester, 2-cyclic ethylene acetal This experiment is carried out with dried twice-distilled hexamethylphosphortriamide (HMPT), anhydrous and peroxide-free tetrahydrofuran (THF) and under a nitrogen atmosphere. An ethereal solution of methyl lithium (25.0 ml., 2.004 M) is concentrated to dryness and pumped in vacuo. Under nitrogen at 1 atm. 46 ml. of THF is added to 2.24 g. of triphenylmethane and the resulting solution is added under nitrogen to the previously prepared methyl lithium at 0°–5°C. The methyl lithium dissolves in 45 minutes and the solution of lithium triphenylmethyl is stirred for 3.5 hours at room temperature under nitrogen. The mixture is diluted with 46 ml. of dry, oxygen-free HMPT at 5°–10°C. and allowed to warm spontaneously to room temperature. The mixture is 0.486 N with respect to lithium triphenylmethyl.

2.684 G. of 2,6-dioxo-4,5,6,7-tetrahydro-3-indanheptanoic acid methyl ester, 2-cyclic ethylene ketal in 25 ml. of dry THF is placed under nitrogen and added dropwise at room temperature to a well stirred solution of lithium triphenylmethyl (16.03 ml., 0.486 N) prepared as previously described. The resulting mixture is added dropwise with stirring to 33 ml. of methyl iodide and the mixture is stirred for 5 minutes at room temperature, poured into a mixture of 6 ml. of acetic acid, 50 ml. of benzene, 50 ml. of hexane and 10 ml. of water, and finally neutralized with 5% aqueous potassium bicarbonate. The layers are separated, the water phase extracted with four 50 ml. portions of benzene and the combined benzene phases are extracted successively with four 75 ml. portions of water and one of saturated salt solution. The benzene solution is dried over Na$_2$SO$_4$ and concentrated to dryness to yield 3.18 g. of 2,6-dioxo-4,5,6,7-tetrahydro-7-methyl-3-inadanheptanoic acid methyl ester, 2-cyclic ethylene ketal.

This product is dissolved in 30 ml. of chloroform and chromatographed over 32 g. of silica gel. Concentration of the product-rich fractions affords pure material nmr (CDCl$_3$) 1.07 (d,3, J=7Hz), 3.40 (s,3), 3.58 (s,4) ppm.

EXAMPLE 7

2,4,5,6,7,7a-Hexahydro-6-hydroxy-7-methyl-2-oxo-3-indeneheptanoic acid methyl ester To 9.285 g. of 2,6-dioxo-4,5,6,7-tetrahydro-7-methyl-3-indanheptanoic acid methyl ester, 2-cyclic ethylene ketal in 100 ml. of tetrahydrofuran under nitrogen, stirred at 0°C. is added dropwise 13.5 g. of lithium tri-t-butoxy aluminum hydride in 250 ml. of tetrahydrofuran. The mixture is stirred at 0°C. for 4 hours following which 100 ml. of saturated aqueous sodium sulfate at 0°C. is slowly added maintaining the mixture at 0°C. The mixture is concentrated in vacuo to remove tetrahydrofuran, the residue filtered to remove salts and the aqueous phase extracted with ethyl acetate. The organic phase is washed with saturated salt solution, dried and concentrated in vacuo to an oil (9.34 g.), of 2-oxo-4,5,6,7-tetrahydro-6-hydroxy-7-methyl-3-indanheptanoic acid methyl ester, 2-cyclic ethylene acetal which is used in the following step.

To the 9.34 g. of ketal ester obtained immediately above in 95 ml. of tetrahydrofuran is added aqueous perchloric acid (95 ml., 1.5 N) with stirring and cooling at 0°–5°C. The mixture is stirred at 10°–15°C. for two hours, poured slowly into saturated aqueous potassium bicarbonate, filtered and the funnel washed with tetrahydrofuran. The filtrate is concentrated in vacuo and the concentrate extracted with ethyl acetate. The combined organic extracts are washed with 1/3 volume of saturated salt solution, dried over MgSO$_4$ and concentrated in vacuo to an oil, (8.37 g.) of 2-oxo-4,5,6,7-tetrahydro-6-hyroxy-7-methyl-3-indanheptanoic acid methyl ester.

To this keto ester (8.37 g.) in 67.2 ml. of methanol under nitrogen and at 20°C. is added dropwise with stirring a precooled solution of potassium hydroxide (5.598 g. in 89.6 ml. of water and 58.2 ml. of methanol). The mixture is stirred at room temperature (25°C.) for 20 hours, concentrated in vacuo, extracted with three 50 ml. portions of ether, cooled to 0°C., and 1 g. of monosodium phosphate added and the mixture acidified with 2.5 N hydrochloric acid. The mixture is extracted with ethyl acetate, the combined organic extracts washed with saturated salt solution, dried over MgSO$_4$ and concentrated in vacuo to near dryness. The residue is flushed once with ether benzene (1:1) and concentrated in vacuo to an oil, (8.57 g.) of 2,4,5,6,7,7a-hexahydro-6-hydroxy-7-methyl-2-oxo-3-indeneheptanoic acid.

The ketol acid (8.57 g.) from the previous reaction is dissolved in 50 ml. of ether and an excess of ethereal diazomethane is added at 0°C. After 30 minutes at 0°–10°C. the mixture is concentrated in vacuo to obtain 8.93 g. of 2,4,5,6,7,7a-hexahydro-6-hydroxy-7-methyl-2-oxo-3-indeneheptanoic acid methyl ester as an oil which is used without further purification. The $\Delta$ $^\alpha$ $^\beta$ ketone has $\lambda_{max}^{CH_3OH}$ 239 $m\mu$, $E_{mol}$ 13,500.

EXAMPLE 8

Cis-6-hydroxy-7-methyl-2-oxo-3-hydrindanheptanoic acid methyl ester

A vigorously stirred solution of 1.31 g. of 2,4,5,6,7,7a-hexahydro-6-hydroxy-7-methyl-2-oxo-3-indeneheptanoic acid methyl ester in 50 ml. of ethanol is hydrogenated over 10% palladium on charcoal at 1 atmosphere and 20°–25°C. When the hyrogenation is complete as determined by disappearance of the 5.9 and 6.2 $\mu$ bands in the ir the catalyst is removed by filtration, washed and the combined filtrates concentrated to dryness in vacuo. The residue is chromatographed over 42 g. of silica gel. Elution with 12% acetone in chloroform yields cis-6-hydroxy-7-methyl-2-oxo-3-hydrindanheptanoic acid methyl ester, $R_F$ = 0.2–0.3 on silica gel (12% acetone in chloroform).

EXAMPLE 9

Cis-3,4,5,7a-tetrahydro-7-methyl-2-oxoindanheptanoic acid methyl ester

A. To a stirred solution of 0.22 g. of 6-hydroxy-7-methyl-2-oxo-3-hydrindanheptanoic acid methyl ester in 1.5 ml. of pyridine under nitrogen at 0°C. is added dropwise a solution of methanesulfonyl chloride (0.740 g., 0.00647 mole) in 1 ml. of pyridine. The mixture is allowed to stand overnight at 0°C., added to ice-water and after 5 minutes extracted with four 25 ml. portions of ether. The combined ethereal extracts are washed successively with cold 1 N hydrochloric acid, cold 5% potassium bicarbonate and saturated sodium chloride, dried (MgSO$_4$ and charcoal) and concentrated to dryness in vacuo. The 6-mesylate of the starting material is obtained as a nearly colorless oil, (0.268 g.) $R_F$ = 0.3 on silica gel (1.5% acetone in chloroform) which is used directly in the next reaction.

B. A solution of 0.268 g. of the mesylate ester obtained immediately above in 3 ml. of dimethyl sulfoxide is maintained under nitrogen at 100°C. for 7 hours. The mixture is then cooled to 5°–10°C. and added to 50 g. of ice-water and extracted with four 50 ml. portions of hexane. The organic extract is washed successively with 4 portions of water of equal volume and 1 portion of saturated salt solution; dried over MgSO$_4$ and concentrated to an oil in vacuo. The residue is purified by chromatography on 20 g. of silica gel. 3,4,5,7a-Tetrahydro-7-methyl-2-oxoindanheptanoic acid methyl ester is eluted with 2% acetone in chloroform. The yield is 0.110g. $R_F$ = 0.5 on silica gel (2% acetone in chloroform), ir (CHCl$_3$) 1745 (C=O) and 1727 cm$^{-1}$ (ester C = O), nmr (CDCl$_3$) 5.50 (m, 1) 3.65 (s, 3), 1.67 (t, 3, J - 1.5 Hz) ppm.

EXAMPLE 10

3-Acetyl-2-[2-benzyloxycarbonyl)ethyl]-5-oxocyclopentane heptanoic acid methyl ester, 5-cyclic ethylene acetal A. A mixture of 0.526 g. of 3,4,5,7a-tetrahydro-7-methyl-2-oxoindanheptanoic acid methyl ester, ethylene glycol (1.5 ml.), p-toluenesulfonic acid monohydrate (25 mg.) and benzene (50 ml.) is refluxed overnight under nitrogen in a flask equipped with a water separator. The mixture is cooled to room temperature, poured into an equal volume of 5% potassium bicarbonate, the layers separated and the aqueous phase extracted with benzene. The combined benzene extracts are extracted twice using equal volumes of saturated salt solution, dried over NaSO$_4$ and concentrated in vacuo to yield 0.58 g. of the 2-cyclic ethylene acetal of the starting material, $R_F$ = 0.7 on silica gel (10% acetone in chloroform) ir (CHCl$_3$), 5.76,10.50 $\mu$.

B. To a stirred solution of 0.375 g. of the immediately preceding product in 33 ml. of t-butanol under nitrogen at 15°C. is added a mixture of potassium carbonate (0.390 g.) sodium periodate (1.58 g.) and potassium permanganate (0.018 g.) in 100 ml. of water. The mixture is stirred at 20°–25°C. for 20 hours, 0.4 ml. of ethylene glycol is added and the mixture concentrated on a water pump until most of the t-butanol is removed. A volume of water equal to the concentrate is added and the mixture extracted with four 25 ml. portions of benzene-ether (1:1) to remove neutral material. The aqueous layer is acidified with monosodium dihydrogenphosphate and extracted with four 50 ml. portions of ethyl acetate, dried over Na$_2$SO$_4$ and concentrated to dryness to yield 0.320 g. of keto acid containing 3-acetyl-2-(2-carboxyethyl)-5-oxycyclopentane heptanoic acid methyl ester, 5-cyclic ethylene acetal. The latter product is dissolved in 3 ml. of anhydrous methanol and 1 ml. of 1.00 M sodium methoxide is added. The pale yellow mixture is kept under nitrogen for 17 hours, then added to excess cold saturated aqueous sodium dihydrogenphosphate and extracted four times with ethyl acetate. The organic extract is dried over Na$_2$SO$_4$ and concentrated to dryness to give trans trans keto acid (12a). To the latter in 5 ml. of ether is added excess ethereal phenyl diazomethane. The orange solution is kept at room temperature overnight. Benzene (5 ml.) is added, the mixture extracted with dilute aqueous potassium bicarbonate, dried over sodium sulfate and concentrated to dryness to give 3-acetyl-2-[2-(benzyloxycarbonyl)ethyl]-5-oxocyclopentane heptanoic acid methyl ester, 5-cyclic ethylene ketal. The latter is purified by chromatography on 20 g. of silica gel, eluting with 7% acetone in chloroform: ir (CHCl$_3$) 5.77, 5.80, 5.83, 10.55 $\mu$; nmr (CDCl$_3$) 7.30 (s,5), 5.07 (s,2), 3.83 (s,4), 3.60 (s,3), 2.09 (s,3) ppm.

EXAMPLE 11

3-Acetoxy-2-[2-(benzyloxycarbonyl)ethyl]-5-oxocyclopentaneheptanoic acid methyl ester, 5-cyclic ethylene acetal Buffered peroxytrifluoracetic acid is prepared as follows: To 10 ml. of methylene chloride stirred at 0°C. is added 1.08 ml. of 90% hydrogen peroxide. Trifluoracetic anhydride (7 ml.) is added over 2–3 minutes. The mixture is allowed to warm to 20°–25°C. and after 20 minutes is cooled to 0°C. Powdered disodium monohydrogen phosphate (7 g.) is added in portions with good stirring. The reagent is kept at 0°C. and by iodometric titration is ~0.3 Molar.

To 510 of 3-acetyl-2[2-(benzyloxycarbonyl)ethyl]-5-oxocyclopentaneheptanoic acid methyl ester, 5-cyclic ethylene ketal in 6 ml. of methylene chloride is added 8.4 g. of Na$_2$ HPO$_4$. To the stirred mixture at 0°C. is added 5 ml. of the buffered 0.3 M peroxytrifluoracetic acid. The stirred mixture is kept at 25°C. After 4 hours 4 ml. of 0.3 M buffered peroxytrifluoracetic acid is added and the mixture stirred overnight. An additional 4 ml. of 0.3 M peroxytrifluoroacetic acid is then added. After 24 hours total time the mixture is chilled, filtered and the precipitate washed with methylene chloride. The filtrate is washed with aqueous sodium bisulfite, aqueous potassium bicarbonate, saturated aqueous sodium chloride, dried over sodium sulfate and concentrated to dryness to give 520 mg. of 3-acetoxy-2-[2(benzyloxycarbonyl)ethyl]-5-oxocyclopentaneheptanoic acid methyl ester, 5-cyclic ethylene acetal: ir(CHCl$_3$) 5.75–5.80, 8.00, 10.55μ; nmr (CDCl$_3$) 1.98 (s,3) ppm.

EXAMPLE 12

3-Acetoxy-2-(2-carboxyethyl)-5-oxocyclopentaneheptanoic acid methyl ester, 5-ethylene acetal A solution of 475 mg. of 3-acetoxy-2-[2(benzyloxycarbonyl)ethyl]-5-oxocyclopentaneheptanoic acid methyl ester, 5-cyclic ethylene ketal in 5 ml. of ethyl acetate is added to a pre-reduced suspension of 250 mg. of 10% Pd/C in 7 ml. of ethyl acetate. Hydrogenation is carried out at 25°C. and atmospheric pressure, and one molar equivalent of hydrogen is consumed in 20 minutes. The mixture is filtered, the precipitate washed with ethyl acetate and the filtrate concentrated to dryness. The residue is dissolved in 20 ml. of ether, 20 ml. of hexane is added and the mixture extracted with aqueous potassium bicarbonate. The latter extract is acidified with powdered NaH$_2$PO$_4$ and extracted with ethyl acetate (4× 30 ml.). The organic extract is dried over Na$_2$SO$_4$ and concentrated to dryness to give 350 mg. of 3-acetoxy-2-(2-carboxyethyl)-5-oxocyclopentaneheptanoic acid methyl ester, 5-cyclic ethylene acetal: ir(neat) 2.8–3.3, 5.78, 5.88, 8.10, 10.55μ.

EXAMPLE 13

3-Acetoxy-2-vinyl-5-oxocyclopentaneheptanoic acid methyl ester, 5-cyclic ethylene acetal To a solution of 380 mg. of 3-acetoxy-2-(2-carboxyethyl)-5-oxocyclopentaneheptanoic acid methyl ester 5-cyclic ethylene acetal in 12 ml. of benzene is added pyridine (240 mg.) Cu(OAc)$_2$.H$_2$O (10 mg.) and lead tetraacetate (440 mg.). Air in the system is displaced with nitrogen and the mixture is stirred in the dark for 30 minutes. With continued stirring it is then photolyzed at 3500 A (temp about 30°C.) in a Rayonet photochemical reactor. After 2 hours ether and cold water are added followed by powdered NaH$_2$PO$_4$. The mixture is extracted with ether, the organic phase washed with water, dilute aqueous KHCO$_3$, and saturated aqueous NaCl. It is dried over Na$_2$SO$_4$ and concentrated to dryness to give 210 mg. of 3-acetoxy-2-vinyl-5-oxocyclopentaneheptanoic acid methyl ester, 5-cyclic ethylene acetal. The product is purified by silica gel chromatography (20 g.) eluting with 7% acetone in chloroform: ir (CHCl$_3$) 5.73, 5.77, 6.20, 8.00, 10.55, 10.85μ.

EXAMPLE 14

3-Acetoxy-2-formyl-5-oxocyclopentaneheptanoic acid methyl ester, 5-cyclic ethylene acetal To a solution of 88 mg. of 3-acetoxy-2-vinyl-5-oxocyclopentaneheptanoic acid methyl ester, 5-cyclic ethylene acetal in 2 ml. of tetrahydrofuran, stirred under nitrogen, is added 0.4 ml. of 1% aqueous osmium tetroxide (4 mg. OsO$_4$). Within 10 minutes the mixture becomes black and 196 mg. of sodium periodate in 1.4 ml. of water is added over 10 minutes. After 2 hours the mixture is filtered, the precipitate of sodium iodate washed with ethyl acetate and the filtrate washed with saturated aqueous sodium chloride. It is dried over Na$_2$SO$_4$, treated with charcoal, filtered, and the nearly colorless filtrate concentrated to dryness to give 70 mg. of 3-acetoxy-2-formyl-5-oxocyclopentaneheptanoic acid methyl ester, 5-cyclic ethylene acetal: ir 3.7, 5.77, 5.80, 10.55 μ.

EXAMPLE 15

3-Acetoxy-2-(3-oxo-1-octenyl)-b 5-oxocyclopentaneheptanoic acid metyl ester, 5-cyclic ethylene acetal 70 Mg. of dimethyl 2-oxoheptylphosphonate in 2 ml. of tetrahydrofuran is added to 12 mg. of 48% sodium hydride in 1 ml. of tetrahydrofuran, and the mixture stirred at 0°C. under nitrogen for 30 minutes. 70 Mg. of 3-acetoxy-2-formyl-5-oxocyclopentaneheptanoic acid methyl ester, 5-cyclic ethylene ketal in 2 ml. of tetrahydrofuran is then added dropwise and the mixture allowed to warm to 20°–25°C. After 3 hours the mixture is chilled, added to cold saturated aqueous NaH$_2$PO$_4$, extracted with ethyl acetate, and the latter extract dried over Na$_2$SO$_4$ and concentrated to dryness. The residue is purified by silica gel chromatography (7.8 g. silica gel), eluting with 7% acetone in chloroform to give 3-acetoxy-2-(3-oxo-1-octenyl)-5-oxocyclopentaneheptanoic acid methyl ester, 5-cyclic ethylene acetal: ir (CHCl$_3$) 5.78, 5.9, 6.0, 6.17, 8.00, 10.55 μ;

U.V. $\lambda_{max}^{CH_3OH}$ 228 mμ(Em 10,050).

EXAMPLE 16

3-Acetoxy-2-(3-hydroxy-1-octenyl)-5-oxocyclopentaneheptanoic acid methyl ester, 5-cyclic ethylene acetal To a solution of 40 mg. of 3-acetoxy-2-(3-oxo-1-octenyl)-5-oxocyclopentaneheptanoic acid methyl ester, 5-cyclic ethylene ketal in 1.5 ml. of methanol stirred under nitrogen at 0°C. is added 0.4 ml. of a solution of 17 mg. of sodium borohydride in 2 ml. of methanol (3.4 mg. NaBH$_4$). After 30 minutes at 0°C. the mixture is added to 20 ml. of cold saturated aqueous NaH$_2$PO$_4$ and extracted with ethyl acetate. The latter extract is dried over Na$_2$SO$_4$ and concentrated to dryness to give 40 mg. of 3-acetoxy-2-(3-hydroxy-1-octenyl)-5-oxocyclopentaneheptanoic acid methyl ester, 5-cyclic ethylene acetal as a mixture of hydroxy epimers on the octenyl side chain. If desired the epimers may be separated at this stage by thin layer chromatography on silica gel (system 10% acetone in chloroform).

EXAMPLE 17

3-Hydroxy-2-(3-hydroxy-1-octenyl)-5-oxocyclopentaneheptanoic acid, 5-cyclic ethylene acetal To a stirred solution of 30 mg. of the mixture of epimers of 3-acetoxy-2-(3-hydroxy-1-octenyl)-5-oxocyclopentaneheptanoic acid methyl ester, 5-cyclic ethylene acetal obtained in the preceding example in 1 ml. of methanol at 0.C. under nitrogen is added 0.4 ml. of a solution of 88 mg. of potassium hydroxide in 1 ml. of water. The yellow solution is kept at 20°–25°C. for 3 hours. It is then added to cold saturated aqueous NaH$_2$PO$_4$ (10 ml.) and extracted with ethyl acetate. The latter extract is dried over Na$_2$SO$_4$ and concentrated to dryness to give 28 mg. of 3-hydroxy-2-(3-hydroxy-1-octenyl)-5-oxocyclopentaneheptanoic acid, 5-cyclic ethylene acetal as a mixture of hydroxy epimers on the octenyl side chain. The substances are separable on silica gel plates (system-benzene: dioxane: acetic acid: 20:20:1), the most polar component ($R_F \sim 0.5$) being the desired one.

EXAMPLE 18

3-Hydroxy-2-(3-hydroxy-1-octenyl)-5-oxocyclopentaneheptanoic acid (±)-prostaglandin $E_1$)

A solution of 30 mg. of the epimeric mixture of 3-hydroxy-2-(3-hydroxy-1-octenyl)-5-oxocyclopentaneheptanoic acid, 5-cyclic ethylene acetal in 2 ml. of 50% aqueous acetic acid is kept at 20°–25°C. for 3 hours. It is then concentrated to dryness to give 28 mg. of crude 3-hydroxy-2-(3-hydroxy-1-octenyl)-5-oxocyclopentaneheptanoic acid, (prostaglandin $E_1$). The product is purified by preparative thin layer chromatography on silica gel (system-benzene: dioxane: acetic acid — 40:40:1) visualizing the components by water spray. The band, which corresponds to prostaglandin $E_1$ is eluted with methanol, the eluate filtered, the filtrate concentrated to dryness and the residue taken up in chloroform. The latter solution is washed with aqueous $NaH_2PO_4$, dried over $Na_2SO_4$ and concentrated to dryness. Crystallization of the residue from ether-hexane gives (±)-prostaglandin $E_1$ m.p. ~110°C. The synthetic material has identical tlc mobility as naturally derived prostaglandin $E_1$.

Various changes and modifications may be made in carrying out the present invention without departing from the spirit and scope thereof. Insofar as these changes and modifications are within the purview of the annexed claims, they are to be considered as part of our invention.

What is claimed is:
1. A compound having the formula

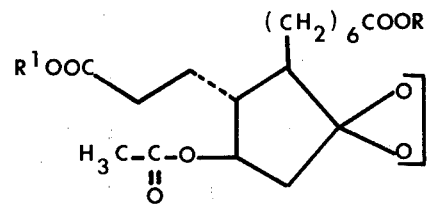

where R is lower alkyl and $R^1$ is hydrogen, benzyl or substituted benzyl.

2. The compound of claim 1 where R is lower alkyl and $R^1$ is hydrogen.

3. The compound of claim 1 where R is methyl and $R^1$ is hydrogen.

4. The process for preparing 3-acetoxy-2(2-carboxyethyl)-5-oxocyclopentane heptanoic acid lower alkyl ester, 5-cyclic ethylene acetal that comprises treating 3-acetoxy-2-[2-(benzyloxycarbonyl)-ethyl]-5-oxocyclopentane heptanoic acid lower alkyl ester, 5-cyclic ethylene acetal with hydrogen in the presence of palladium catalyst.

* * * * *